(12) United States Patent
Baker et al.

(10) Patent No.: US 6,482,626 B2
(45) Date of Patent: Nov. 19, 2002

(54) HUMAN DNASE

(75) Inventors: Kevin P. Baker, San Mateo, CA (US); Will F. Baron, Brisbane, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/074,509

(22) Filed: Feb. 11, 2002

(65) Prior Publication Data

US 2002/0142437 A1 Oct. 3, 2002

Related U.S. Application Data

(63) Continuation of application No. 09/643,520, filed on Aug. 22, 2000, now abandoned, and a continuation of application No. 08/794,827, filed on Feb. 4, 1997, now abandoned.
(60) Provisional application No. 60/109,796, filed on Feb. 5, 1996.

(51) Int. Cl.⁷ .............................. C12N 15/55; C12N 9/22
(52) U.S. Cl. .................... 435/199; 435/320.1; 435/366; 435/369; 536/23.2
(58) Field of Search .............................. 435/199, 320.1, 435/366, 369; 536/23.2

(56) References Cited

FOREIGN PATENT DOCUMENTS

| WO | WO 90/07572 | * | 7/1990 |
|----|-------------|---|--------|
| WO | WO 93/25670 | * | 12/1993 |

OTHER PUBLICATIONS

Baron, W.F. et al. *Gene* 215:291–301 (1998).*

Parrish et al., "A muscle–specific DNase I–like gene in human Xq28" *Human Molecular Genetics* 4 (9) :1557–1564 (1995).*

Rodriguez, A. et al., "Identification, localization, and expression of two novel human genes similar to deoxyribonuclease I" *Genomics* (EMBL databank Accession No. U56814) 42:507–513 (1997).*

Zeng, Z. et al. *Biochem. & Biophys. Res. Comm.* 231:499–504 (1997).*

* cited by examiner

Primary Examiner—Charles L. Patterson, Jr.
(74) Attorney, Agent, or Firm—David W Evans

(57) ABSTRACT

This invention relates to a novel human deoxyribonuclease, referred to as LS-DNase, that is relatively resistant to inhibition by actin, as compared to human DNase I. The invention provides nucleic acid sequences encoding LS-DNase, thereby enabling the production of LS-DNase by recombinant DNA methods in quantities sufficient for clinical use. The invention also relates to pharmaceutical compositions and therapeutic uses of LS-DNase.

7 Claims, 4 Drawing Sheets

```
  1 GAATTCGGCACGAGAGCACTCCAAGCACTGCTGTCTTCTCACAGAGTCTTGAAGCCAGAG

61 CAGCGCCAGG ATG TCA CGG GAG CTG GCC CCA CTG CTG CTT CTC CTC
-20            Met Ser Arg Glu Leu Ala Pro Leu Leu Leu Leu Leu

107 CTC TCC ATC CAC AGC GCC CTG GCC ATG AGG ATC TGC TCC TTC AAC
 -8 Leu Ser Ile His Ser Ala Leu Ala Met Arg Ile Cys Ser Phe Asn

152 GTC AGG TCC TTT GGG GAA AGC AAG CAG GAA GAC AAG AAT GCC ATG
  8 Val Arg Ser Phe Gly Glu Ser Lys Gln Glu Asp Lys Asn Ala Met

197 GAT GTC ATT GTG AAG GTC ATC AAA CGC TGT GAC ATC ATA CTC GTG
 23 Asp Val Ile Val Lys Val Ile Lys Arg Cys Asp Ile Ile Leu Val

242 ATG GAA ATC AAG GAC AGC AAC AAC AGG ATC TGC CCC ATA CTG ATG
 38 Met Glu Ile Lys Asp Ser Asn Asn Arg Ile Cys Pro Ile Leu Met

287 GAG AAG CTG AAC AGA AAT TCA AGG AGA GGC ATA ACG TAC AAC TAT
 53 Glu Lys Leu Asn Arg Asn Ser Arg Arg Gly Ile Thr Tyr Asn Tyr

332 GTG ATT AGC TCT CGG CTT GGA AGA AAC ACA TAT AAA GAA CAA TAT
 68 Val Ile Ser Ser Arg Leu Gly Arg Asn Thr Tyr Lys Glu Gln Tyr

377 GCC TTT CTC TAC AAG GAA AAG CTG GTG TCT GTG AAG AGG AGT TAT
 83 Ala Phe Leu Tyr Lys Glu Lys Leu Val Ser Val Lys Arg Ser Tyr

422 CAC TAC CAT GAC TAT CAG GAT GGA GAC GCA GAT GTG TTT TCC AGG
 98 His Tyr His Asp Tyr Gln Asp Gly Asp Ala Asp Val Phe Ser Arg

467 GAG CCC TTT GTG GTC TGG TTC CAA TCT CCC CAC ACT GCT GTC AAA
113 Glu Pro Phe Val Val Trp Phe Gln Ser Pro His Thr Ala Val Lys

512 GAC TTC GTG ATT ATC CCC CTG CAC ACC ACC CCA GAG ACA TCC GTT
128 Asp Phe Val Ile Ile Pro Leu His Thr Thr Pro Glu Thr Ser Val

557 AAG GAG ATC GAT GAG TTG GTT GAG GTC TAC ACG GAC GTG AAA CAC
143 Lys Glu Ile Asp Glu Leu Val Glu Val Tyr Thr Asp Val Lys His

602 CGC TGG AAG GCG GAG AAT TTC ATT TTC ATG GGT GAC TTC AAT GCC
158 Arg Trp Lys Ala Glu Asn Phe Ile Phe Met Gly Asp Phe Asn Ala

647 GGC TGC AGC TAC GTC CCC AAG AAG GCC TGG AAG AAC ATC CGC TTG
173 Gly Cys Ser Tyr Val Pro Lys Lys Ala Trp Lys Asn Ile Arg Leu

692 AGG ACT GAC CCC AGG TTT GTT TGG CTG ATC GGG GAC CAA GAG GAC
188 Arg Thr Asp Pro Arg Phe Val Trp Leu Ile Gly Asp Gln Glu Asp

737 ACC ACG GTG AAG AAG AGC ACC AAC TGT GCA TAT GAC AGG ATT GTG
203 Thr Thr Val Lys Lys Ser Thr Asn Cys Ala Tyr Asp Arg Ile Val

782 CTT AGA GGA CAA GAA ATC GTC AGT TCT GTT GTT CCC AAG TCA AAC
218 Leu Arg Gly Gln Glu Ile Val Ser Ser Val Val Pro Lys Ser Asn

827 AGT GTT TTT GAC TTC CAG AAA GCT TAC AAG CTG ACT GAA GAG GAG
233 Ser Val Phe Asp Phe Gln Lys Ala Tyr Lys Leu Thr Glu Glu Glu
```

FIG._1a

```
872  GCC CTG GAT GTC AGC GAC CAC TTT CCA GTT GAA TTT AAA CTA CAG
248  Ala Leu Asp Val Ser Asp His Phe Pro Val Glu Phe Lys Leu Gln

917  TCT TCA AGG GCC TTC ACC AAC AGC AAA AAA TCT GTC ACT CTA AGG
263  Ser Ser Arg Ala Phe Thr Asn Ser Lys Lys Ser Val Thr Leu Arg

962  AAG AAA ACA AAG AGC AAA CGC TCC TAGACCCAAGGGTCTCATCTTATTAAC
278  Lys Lys Thr Lys Ser Lys Arg Ser

1013 CATTTCTTGCCTCTAAATAAAATGTCTCTAACAAAAAAAAAAAAAAAAAAAAAAAAAAA

1073 ACTCGAG
```

FIG._1b

```
hu.LS.DNase    1  MRICSFNVRSFGES KQEDKNAMDVIVKVIKRCDIHLVMEIKDSNNRICPI
hu.DNase1      1  LKIAAFNIQTFGET KMSNATLVSYIVQIL SRYDIALVQEVRDSHLTAVGK hu.LS.DNase   51  LMEKLNRNSRRGITYNYVISSRLGRNTYKEQYAFLYKEKLVSVKRSYHYH
hu.DNase1     51  LLDNLNQDAPD--TYHVVSEPLGRNSYKERYLFVYRPDQSAVDSYYYD hu.LS.DNase  101  D-YQDGDADVFSREPFVVWFQSPHTAVKDFVHIPLHTTPETSVKEIDELV
huDNase1      99  DGCEPCGNDTFNREPAIVRFFSRFTEVREFAHVPLHAAPGDAVAEIDALY hu.LS.DNase  150  EVYTDVKHRWKAENFIFMGDFNAGCSYVPKKAWKNIRLRTDPRFVWLIGD
hu.DNase1    149  DVYLDVQEKWGLEDVMLMGDFNAGCSYVRPSQWSSIRLWTSPTFQWLIPD hu.LS.DNase  200  QEDTTVKKSTNCAYDRIVLRGQEIVSSVVPKSNVFDFQKAYKLTEEEAL
hu.DNase1    199  SADTTA-TPTHCAYDRIVVAGMLLRGAVVPDSALPENFQAAYGLSDQLAQ hu.LS.DNase  250  DVISDHFPVEFKLQSSRAFTNSKKSVTLRKKTKSKRS
hu.DNase1    248  AISDHYPVEVMLK
```

FIG._2

```
   1 GAATTCCGGCCCATTACCTTCATTTCCTTGGGGATTGAAACGCGTGATGG
  51 TGAGTTCCTCAGAGAAGTGAAAGTGACCTAGAGGGATCCAGTAATTCCTG
 101 TTATCAGCCTGCTTTATAAGTCAGTGAGCCAGGCACTGTCTTCATCCAGC
 151 CTGAAGTCCCAGGAGTGCAAGATGTCCCTGCACCCAGCTTCCCCACGCC
                              ▲
 201 TGGCCTCCCTGCTGCTCTTCATCCTTGCCCTCCATGACACCCTGGCCCTA
 251 AGGCTCTGCTCCTTCAATGTGAGGTCCTTTGGAGCGAGCAAGAAGGAAAA
 301 CCATGAAGCCATGGATATCATTGTGAAGATCATCAAACGCTGTGACCTTA
 351 TACTGTTGATGGAAATCAAGGACAGCAGCAACAACATCTGTCCCATGCTG
 401 ATGGAGAAGCTGAATGGAAATTCACGAAGAAGCACAACATACAACTATGT
 451 GATTAGTTCTCGACTTGGAAGAAACACGTACAAAGAGCAGTATGCCTTCG
 501 TCTACAAGGAGAAGCTGGTGTCTGTGAAGACAAAATACCACTACCATGAC
 551 TATCAGGATGGAGACACAGACGTGTTTTCCAGGGAGCCCTTTGTGGTTTG
 601 GTTCCATTCCCCCTTTACTGCTGTCAAGGACTTCGTGATTGTCCCCTTGC
 651 ACACAACTCCCGAGACCTCCGTTAAAGAGATAGATGAGCTGGTCGATGTC
 701 TACACGGATGTGAGAAGCCAGTGGAAGACAGAGAATTTCATCTTCATGGG
 751 TGATTTCAACGCCGGCTGTAGCTATGTCCCCAAGAAGGCCTGGCAGAACA
 801 TTCGTTTGAGGACGGACCCCAAGTTTGTTTGGCTGATTGGGGACCAAGAG
 851 GACACTACGGTCAAGAAGAGTACCAGCTGTGCCTATGACAGGATTGTGCT
 901 TTGTGGACAAGAGATAGTCAACTCCGTGGTTCCCCGTTCCAGTGGCGTCT
 951 TTGACTTTCAGAAAGCTTATGACTTGTCTGAGGAGGAGGCCCTGGATGTC
1001 AGTGATCACTTTCCAGTTGAGTTTAAGCTACAGTCTTCAAGGGCCTTCAC
1051 CAACAACAGAAAATCTGTTTCTCTCAAAAGAGAAAAAAGGCAATCGCT
1101 CCTAGGTATCACGCTCCGGAATTC
```

HUMAN DNASE

RELATED APPLICATION

This is a non-provisional application filed under 37 CFR 1.53 (b) (1), claiming priority to and is a continuation of application Ser. No. 09/643,520, filed Aug. 22, 2000, now abandoned, and Ser. No. 08/794,827, filed Feb. 4, 1997 now abandoned, under 35 USC §120, and claiming priority under USC Section 119(e) to provisional Application Ser. No. 60/109,796 filed on Feb. 5, 1996.

FIELD OF THE INVENTION

The present invention relates to newly identified human deoxyribonuclease (DNase) protein, nucleic acid encoding such protein, the use of such protein and nucleic acid, as well as the production of such protein and nucleic acid, for example, by recombinant DNA methods.

BACKGROUND OF THE INVENTION

Deoxyribonuclease (DNase) is a phosphodiesterase capable of hydrolyzing polydeoxyribonucleic acid, and is known to occur in several molecular forms. Based on their biochemical properties and enzymatic activities, DNase proteins have been classified as two types, DNase I and DNase II. DNase I proteins have a pH optimum near neutrality, an obligatory requirement for divalent cations, and produce 5'-phosphate nucleotides on hydrolysis of DNA. DNase II proteins exhibit an acid pH optimum, can be activated by divalent cations, and produce 3'-phosphate nucleotides on hydrolysis of DNA.

DNase from various species have been purified to a varying degree. For example, various forms of bovine DNase I have been purified and completely sequenced (Liao, et al., J. Biol. Chem. 248:1489–1495 (1973); Oefner, et al., J. Mol. Biol. 192:605–632 (1986); Lahm, et al., J. Mol. Biol. 221:645–667 (1991)), and DNA encoding bovine DNase I has been cloned and expressed (Worrall, et al., J. Biol. Chem 265:21889–21895 (1990)). Porcine and orcine DNase I proteins also have been purified and completely sequenced (Paudel, et al., J. Biol. Chem. 261:16006–16011 (1986); Paudel, et al., J. Biol. Chem. 261:16012–16017 (1986)).

DNA encoding a human DNase I has been isolated and sequenced and the DNA has been expressed in recombinant host cells, thereby enabling the production of human DNase I in commercially useful quantities. Shak, et al., Proc. Natl. Acad. Sci. 87:9188–9192 (1990). The term "human DNase I" will be used hereafter to refer to the mature polypeptide disclosed in Shak, et al.

DNA encoding other polypeptides having homology to human DNase I also have been identified. Rosen, et al., PCT Patent Publication No. WO 95/30428, published Nov. 16, 1995; Parrish, et al., Hum. Mol. Genet. 4:1557–1564 (1995).

DNase I has a number of known utilities and has been used for therapeutic purposes. Its principal therapeutic use has been to reduce the viscoelasticity of pulmonary secretions (mucus) in such diseases as pneumonia and cystic fibrosis (CF), thereby aiding in the clearing of respiratory airways. See e.g., Lourenco, et al., Arch. Intern. Med. 142:2299–2308 (1982); Shak, et al., Proc. Natl. Acad. Sci. 87:9188–9192 (1990); Hubbard, et al., New Engl. J. Med. 326:812–815 (1992); Fuchs, et al., New Engl. J. Med. 331:637–642 (1994); Bryson, et al., Drugs 48:894–906 (1994). Mucus also contributes to the morbidity of chronic bronchitis, asthmatic bronchitis, bronchiectasis, emphysema, acute and chronic sinusitis, and even the common cold.

The pulmonary secretions of persons having such diseases are complex materials, that include mucus glycoproteins, mucopolysaccharides, proteases, actin, and DNA. DNase I is effective in reducing the viscoelasticity of pulmonary secretions by hydrolyzing, or degrading, high-molecular-weight DNA that is present in such secretions. Shak, et al., Proc. Natl. Acad. Sci. 87:9188–9192 (1990); Aitken, et al., J. Am. Med. Assoc. 267:1947–1951 (1992). The DNA-hydrolytic activity of DNase I in pulmonary secretions may be reduced, however, as a result of the interaction of the DNase I with actin. Lazarides, et al., Proc. Natl. Acad. Sci. 71:4742–4746 (1974); Mannherz, et al., Eur. J. Biochem. 104:367–379 (1980). Accordingly, forms of DNase I that bind actin with lower affinity than human native DNase I, but that still possess DNA-hydrolytic activity should be useful therapeutic agents, especially in the treatment of patients having pulmonary secretions that comprise relatively large amounts of actin. Variants of human DNase I having reduced affinity for actin have been prepared synthetically and shown to be more potent than the native enzyme in reducing the viscosity of sputum of cystic fibrosis patients. Lazarus, et al., U.S. patent application Ser. No. 08/540,527 (filed Oct. 9, 1995).

SUMMARY OF THE INVENTION

The present invention provides a novel DNase, as well as analogs and variants thereof, that have DNA-hydrolytic activity but that are resistant to inhibition by actin. This novel polypeptide, referred to as LS-DNase, is of human origin.

The invention also provides nucleic acids encoding LS-DNase, recombinant vectors comprising such nucleic acids, recombinant host cells transformed with those nucleic acids or vectors, and processes for producing LS-DNase by means of recombinant DNA technology. The invention includes the use of such nucleic acids and vectors for in vivo or ex vivo gene therapy.

The invention also provides pharmaceutical compositions comprising LS-DNase, optionally together with a pharmaceutically acceptable excipient, as well as substantially purified antibodies that are capable of binding to LS-DNase.

The invention also provides methods for reducing the viscoelasticity or viscous consistency of DNA-containing material in a patient, comprising administering a therapeutically effective dose of LS-DNase to the patient. The invention is particularly directed to a method of treating a patient having a disease such as cystic fibrosis, chronic bronchitis, pneumonia, bronchiectasis, emphysema, asthma, or systemic lupus erythematosus, that comprises administering a therapeutically effective amount of LS-DNase to the patient. The invention also is directed to the use of LS-DNase in in vitro diagnostic assays of a viscous material (e.g., sputum) from a patient.

These and other aspects of the invention will be apparent to the ordinary skilled artisan upon consideration of the following detailed description.

BRIEF DESCRIPTION OF THE FIGURES

FIG. 1 shows the nucleotide sequence (SEQ. ID. NO: 1) and deduced amino acid sequence (SEQ. ID. NO: 2) of LS-DNase. The predicted leader (signal) amino acid sequence is underlined and the start of the mature protein is indicated by the arrowhead.

FIG. 2 shows an alignment of the amino acid sequences of human LS-DNase (SEQ. ID. NO: 3) and human DNase I (SEQ. ID. NO: 4). Identical amino acid residues are boxed, conservative amino acid substitutions are indicated by a dot (•), and conserved cysteine residues are indicated by arrowheads. Two potential glycosylations sites in human DNase I are indicated by asterisks (*). Amino acid residues of human DNase I that are involved in actin binding are shaded. Conserved catalytic residues are in inverted text (white on black).

FIG. 3 shows the nucleotide sequence (SEQ. ID. NO: 11) of murine LS-DNase. The ATG start codon for the predicted protein is indicated by the arrowhead, and the nucleotide sequence encoding the predicted leader (signal) amino acid sequence of the protein is underlined.

DETAILED DESCRIPTION

The various aspects of the present invention are accomplished by first providing isolated DNA comprising the nucleotide coding sequence for LS-DNase. By providing the full nucleotide coding sequence for LS-DNase, the invention enables the production of LS-DNase by means of recombinant DNA technology, thereby making available for the first time sufficient quantities of substantially pure LS-DNase protein for diagnostic and therapeutic uses.

As used herein, the term "LS-DNase" refers to the polypeptide having the amino acid sequence of the mature protein set forth in FIG. 1, as well as modified and variant forms thereof as described herein. The term "human LS-DNase" refers to the polypeptide having the amino acid sequence of the mature protein set forth in FIG. 1.

Modified and variant forms of LS-DNase are produced in vitro by means of chemical or enzymatic treatment or in vivo by means of recombinant DNA technology. Such polypeptides differ from human LS-DNase, for example, by virtue of one or more amino acid substitutions, insertions, and/or deletions, or in the extent or pattern of glycosylation, but substantially retain a biological activity of LS-DNase. Preferably, the modified and variant forms of LS-DNase have DNA-hydrolytic activity that is substantially the same as that of human LS-DNase.

A "variant" or "amino acid sequence variant" of LS-DNase is a polypeptide that comprises an amino acid sequence different from that of human LS-DNase. Generally, a variant will possess at least 80% sequence identity (homology), preferably at least 90% sequence identity, more preferably at least 95% sequence identity, and most preferably at least 98% sequence identity with human LS-DNase. Percentage sequence identity is determined, for example, by the Fitch, et al., Proc. Natl. Acad. Sci. USA 80:1382–1386 (1983), version of the algorithm described by Needleman, et al., J. Mol. Biol. 48:443–453 (1970), after aligning the sequences to provide for maximum homology. Such variants include naturally occurring allelic forms of human LS-DNase that are of human origin as well as natuarlly occurring homologs of human LS-DNase that are found in other animal species.

"DNA-hydrolytic activity" refers to the enzymatic activity of a DNase in hydrolyzing (cleaving) substrate DNA to yield 5'-phosphorylated oligonucleotide end products. DNA-hydrolytic activity is readily determined by any of several different methods known in the art, including analytical polyacrylamide and agarose gel electrophoresis, hyperchromicity assay (Kunitz, J. Gen. Physiol. 33:349–362 (1950); Kunitz, J. Gen. Physiol. 33:363–377 (1950)), or methyl green assay (Kurnick, Arch. Biochem. 29:41–53 (1950); Sinicropi, et al., Anal. Biochem. 222:351–358 (1994)).

For convenience, substitutions, insertions, and/or deletions in the amino acid sequence of human LS-DNase are usually made by introducing mutations into the corresponding nucleotide sequence of the DNA encoding human LS-DNase, for example by site-directed mutagenesis. Expression of the mutated DNA then results in production of the variant LS-DNase, having the desired amino acid sequence.

Whereas any technique known in the art can be used to perform site-directed mutagenesis, e.g. as disclosed in Sambrook, et al., *Molecular Cloning: A Laboratory Manual*, Second Edition (Cold Spring Harbor Laboratory Press, New York (1989)), oligonucleotide-directed mutagenesis is the preferred method for preparing the LS-DNase variants of this invention. This method, which is well known in the art (Zoller, et al., Meth. Enzymol. 100:4668–500 (1983); Zoller, et al., Meth. Enzymol. 154:329–350 (1987); Carter, Meth. Enzymol. 154:382–403 (1987); Kunkel, et al., Meth. Enzymol. 154:367–382 (1987); Horwitz, et al., Meth. Enzymol. 185:599–611 (1990)), is particularly suitable for making substitution variants, although it may also be used to conveniently prepare deletion and insertion variants, as well as variants having multiple substitution, insertion, and/or deletion mutations.

Briefly, in carrying out site-directed mutagenesis of DNA encoding human LS-DNase (or a variant thereof), the DNA is altered by first hybridizing an oligonucleotide encoding the desired mutation to a single strand of the DNA. After hybridization, a DNA polymerase is used to synthesize an entire second strand, using the hybridized oligonucleotide as a primer, and using the single strand of the DNA as a template. Thus, the oligonucleotide encoding the desired mutation is incorporated in the resulting double-stranded DNA.

Oligonucleotides may be prepared by any suitable method, such as by purification of a naturally occurring DNA or by in vitro synthesis. For example, oligonucleotides are readily synthesized using various techniques in organic chemistry, such as described by Narang, et al., Meth. Enzymol. 68:90–98 (1979); Brown, et al., Meth. Enzymol. 68:109–151 (1979); Caruthers, et al., Meth. Enzymol. 154:287–313 (1985). The general approach to selecting a suitable oligonucleotide for use in site-directed mutagenesis is well known. Typically, the oligonucleotide will contain 10–25 or more nucleotides, and will include at least 5 nucleotides on either side of the sequence encoding the desired mutation so as to ensure that the oligonucleotide will hybridize preferentially at the desired location to the single-stranded DNA template molecule.

"Polymerase chain reaction," or "PCR," generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridizing preferentially to a template nucleic acid.

PCR mutagenesis (Higuchi, in *PCR Protocols*, pp.177–183 (Academic Press, 1990); Vallette, et al., Nuc. Acids Res. 17:723–733 (1989)) is also suitable for making the variants of LS-DNase. Briefly, when small amounts of template DNA are used as starting material in a PCR, primers that differ slightly in sequence from the corresponding region in the template DNA can be used to generate relatively large quantities of a specific DNA fragment that differs from the template sequence only at the positions where the primers differ from the template. For introduction of a mutation into a plasmid DNA, for example, the sequence of one of the primers includes the desired mutation and is designed to hybridize to one strand of the plasmid DNA at the position of the mutation; the sequence of the other primer must be identical to a nucleotide sequence within the opposite strand of the plasmid DNA, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. Wagner, et al., in PCR Topics, pp.69–71 (Springer-Verlag, 1991).

If the ratio of template to product amplified DNA is extremely low, the majority of product DNA fragments incorporate the desired mutation(s). This product DNA is used to replace the corresponding region in the plasmid that served as PCR template using standard recombinant DNA methods. Mutations at separate positions can be introduced simultaneously by either using a mutant second primer, or performing a second PCR with different mutant primers and ligating the two resulting PCR fragments simultaneously to the plasmid fragment in a three (or more)-part ligation.

Another method for preparing variants, cassette mutagenesis, is based on the technique described by Wells et al., Gene, 34:315–323 (1985). The starting material is the plasmid (or other vector) comprising the DNA sequence to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. The resulting plasmid contains the mutated DNA sequence.

The presence of mutation(s) in a DNA is determined by methods well known in the art, including restriction mapping and/or DNA sequencing. A preferred method for DNA sequencing is the dideoxy chain termination method of Sanger, et al., Proc. Natl. Acad. Sci. USA 72:3918–3921 (1979).

DNA encoding LS-DNase is inserted into a replicable vector for further cloning or expression. "Vectors" are plasmids and other DNAs that are capable of replicating within a host cell, and as such, are useful for performing two functions in conjunction with compatible host cells (a vector-host system). One function is to facilitate the cloning of nucleic acid that encodes LS-DNase, i.e., to produce usable quantities of the nucleic acid. The other function is to direct the expression of LS-DNase. One or both of these functions are performed by the vector in the particular host cell used for cloning or expression. The vectors will contain different components depending upon the function they are to perform.

The LS-DNase of the present invention may be in the form of a preprotein wherein the DNase includes a leader or signal sequence, or may be in the form of a mature protein which lacks a leader or signal sequence. The LS-DNase also may be in the form of a fusion protein wherein additional amino acid residues are covalently joined to the amino- or carboxy-terminus of the preprotein or mature form of the DNase.

To produce LS-DNase, an expression vector will comprise DNA encoding LS-DNase, as described above, operably linked to a promoter and a ribosome binding site. The LS-DNase then is expressed directly in recombinant cell culture, or as a fusion with a heterologous polypeptide, preferably a signal sequence or other polypeptide having a specific cleavage site at the junction between the heterologous polypeptide and the LS-DNase amino acid sequence.

"Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

Prokaryotes (e.g., E. coli, strains of Bacillus, Pseudomonas, and other bacteria) are the preferred host cells for the initial cloning steps of this invention. They are particularly useful for rapid production of large amounts of DNA, for production of single-stranded DNA templates used for site-directed mutagenesis, and for DNA sequencing of the variants generated. Prokaryotic host cells also may be used for expression of DNA encoding LS-DNase. Polypeptides that are produced in prokaryotic cells typically will be non-glycosylated.

In addition, LS-DNase may be expressed in eukaryotic host cells, including eukaryotic microbes (e.g., yeast) or cells derived from an animal or other multicellular organism (e.g., Chinese hamster ovary cells, and other mammalian cells), or in live animals (e.g., cows, goats, sheep). Insect cells also may be used.

Cloning and expression methodologies are well known in the art. Examples of prokaryotic and eukaryotic host cells, and starting expression vectors, suitable for use in producing LS-DNase are, for example, those disclosed in Shak, PCT Patent Publication No. WO 90/07572, published Jul. 12, 1990. To obtain expression of LS-DNase, an expression vector of the invention is introduced into host cells by transformation or transfection, and the resulting recombinant host cells are cultured in conventional nutrient media, modified as appropriate for inducing promoters, selecting recombinant cells, or amplifying LS-DNase DNA. The culture conditions, such as temperature, pH, and the like, are those previously used with the host cell, and as such will be apparent to the ordinarily skilled artisan.

"Transformation" and "transfection" are used interchangeably to refer to the process of introducing DNA into a cell. Following transformation or transfection, the DNA may integrate into the host cell genome, or may exist as an extrachromosomal element. If prokaryotic cells or cells that contain substantial cell wall constructions are used as hosts, the preferred methods of transfection of the cells with DNA is the calcium treatment method described by Cohen et al., Proc. Natl. Acad. Sci. 69:2110–2114 (1972) or the polyethylene glycol method of Chung et al., Nuc. Acids. Res. 16:3580 (1988). If yeast are used as the host, transfection is generally accomplished using polyethylene glycol, as taught by Hinnen, Proc. Natl. Acad. Sci. U.S.A., 75: 1929–1933 (1978). If mammalian cells are used as host cells, transfection generally is carried out by the calcium phosphate precipitation method, Graham, et al., Virology 52:546 (1978), Gorman, et al., DNA and Protein Eng. Tech. 2:3–10 (1990). However, other known methods for introducing DNA into prokaryotic and eukaryotic cells, such as nuclear injection, electroporation, or protoplast fusion also are suitable for use in this invention.

Particularly useful in this invention are expression vectors that provide for the transient expression in mammalian cells of DNA encoding LS-DNase. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Wong, et al., Science 228:810–815 (1985); Lee, et al., Proc. Nat Acad. Sci. USA 82:4360–4364 (1985); Yang, et al., Cell 47:3–10 (1986). Thus, transient expression systems are conveniently used for expressing the DNA encoding amino acid sequence variants of LS-DNase, in conjunction with assays to identify those variants that have such useful properties as increased half-life or decreased immunogenicity in vivo, increased DNA hydrolytic activity, or increased resistance to inhibition by actin. The inhibition of DNase activity by actin is readily determined using assays and methods known in the art and as described herein.

LS-DNase preferably is secreted from the host cell in which it is expressed, in which case the variant is recovered from the culture medium in which the host cells are grown. In that case, it may be desirable to grow the cells in a serum free culture medium, since the absence of serum proteins and other serum components in the medium may facilitate purification of the variant. If it is not secreted, then the LS-DNase is recovered from lysates of the host cells. When the LS-DNase is expressed in a host cell other than one of human origin, the variant will be completely free of proteins of human origin. In any event, it will be necessary to purify the LS-DNase from recombinant cell proteins in order to obtain substantially homogeneous preparations of the LS-DNase. For therapeutic uses, the purified LS-DNase preferably will be greater than 99% pure (i.e., any other proteins will comprise less than 1% of the total protein in the purified composition).

It is further contemplated that LS-DNase may be produced by a method involving homologous recombination and amplification, for example, as described in PCT Patent Publication No. WO 91/06667, published May 16, 1991. Briefly, this method involves transforming cells containing an endogenous gene encoding LS-DNase with a homologous DNA, which homologous DNA comprises (1) an amplifiable gene (e.g., a gene encoding dihydrofolate reductase (DHFR)), and (2) at least one flanking sequence, having a length of at least about 150 base pairs, which is homologous with a nucleotide sequence in the cell genome that is within or in proximity to the gene encoding LS-DNase. The transformation is carried out under conditions such that the homologous DNA integrates into the cell genome by recombination. Cells having integrated the homologous DNA then are subjected to conditions which select for amplification of the amplifiable gene, whereby the LS-DNase gene amplified concomitantly. The resulting cells then are screened for production of desired amounts of LS-DNase. Flanking sequences that are in proximity to a gene encoding LS-DNase are readily identified, for example, by the method of genomic walking, using as a starting point the nucleotide sequence of LS-DNase shown in FIG. 1. Spoerel, et al., Meth. Enzymol. 152:598–603 (1987).

Generally, purification of LS-DNase is accomplished by taking advantage of the differential physicochemical properties of the LS-DNase as compared to the contaminants with which it may be associated. For example, as a first step, the culture medium or host cell lysate is centrifuged to remove particulate cell debris. The LS-DNase thereafter is purified from contaminant soluble proteins and polypeptides, for example, by ammonium sulfate or ethanol precipitation, gel filtration (molecular exclusion chromatography), ion-exchange chromatography, hydrophobic chromatography, immunoaffinity chromatography (e.g., using a column comprising anti-LS-DNase antibodies coupled to Sepharose), tentacle cation exchange chromatography (Frenz, et al., U.S. Pat. No. 5,279,823, issued Jan. 18, 1994), reverse phase HPLC, and/or gel electrophoresis.

In some host cells (especially bacterial host cells) the LS-DNase may be expressed initially in an insoluble, aggregated form (referred to in the art as "refractile bodies" or "inclusion bodies") in which case it will be necessary to solubilize and renature the LS-DNase in the course of its purification. Methods for solubilizing and renaturing recombinant protein refractile bodies are known in the art (see e.g., Builder, et al., U.S. Pat. No. 4,511,502, issued Apr. 16, 1985).

In another embodiment of this invention, covalent modifications are made directly to LS-DNase to give it a desired property (for example, increased half-life or decreased immunogenicity in vivo, increased DNA hydrolytic activity, or increased resistance to inhibition by actin), and may be made instead of or in addition to the amino acid sequence substitution, insertion, and deletion mutations described above.

Covalent modifications are introduced by reacting targeted amino acid residues of LS-DNase with an organic derivatizing agent that is capable of reacting with selected amino acid side-chains or N- or C-terminal residues. Suitable derivatizing agents and methods are well known in the art. Covalent coupling of glycosides to amino acid residues of the protein may be used to modify or increase the number or profile of carbohydrate substituents.

The covalent attachment of agents such as polyethylene glycol (PEG) or human serum albumin to LS-DNase may reduce immunogenicity and/or toxicity of the LS-DNase and/or prolong its half-life, as has been observed with other proteins. Abuchowski, et al., J. Biol. Chem. 252:3582–3586 (1977); Poznansky, et al., FEBS Letters 239:18–22 (1988); Goodson, et al., Biotechnology 8:343–346 (1990); Katre, J. Immunol. 144:209–213 (1990); Harris, *Polyethylene Glycol Chemistry* (Plenum Press, 1992). In addition, modification of LS-DNase by these agents at or adjacent to (i.e., within about five amino acid residues of) an amino acid residue that affects actin binding may produce a variant having increased resistance to inhibition by actin. As another example, the variant or modified form of LS-DNase may comprise an amino acid sequence mutation or other covalent modification that reduces the susceptibility of the variant to degradation by proteases (e.g., neutrophil elastase) that may be present in sputum and other biological materials, as compared to human LS-DNase.

Antibodies to LS-DNase are produced by immunizing an animal with LS-DNase or a fragment thereof, optionally in conjunction with an immunogenic polypeptide, and thereafter recovering antibodies from the serum of the immunized animals. Alternatively, monoclonal antibodies are prepared from cells of the immunized animal in conventional fashion. The antibodies also can be made in the form of chimeric (e.g., humanized) or single chain antibodies or Fab fragments, using methods well known in the art. Preferably, the antibodies will bind to LS-DNase but will not substantially bind to (i.e., cross react with) other DNase proteins (such as human and bovine DNase I). The antibodies can be used in methods relating to the localization and activity of LS-DNase, for example, for detecting LS-DNase and measuring its levels in tissues or clinical samples. Immobilized anti-LS-DNase antibodies are particularly useful in the detection of LS-DNase in clinical samples for diagnostic purposes, and in the purification of LS-DNase.

Purified LS-DNase is used to reduce the viscoelasticity of DNA-containing material, such as sputum, mucus, or other pulmonary secretions. LS-DNase is particularly useful for the treatment of patients with pulmonary disease who have abnormal viscous or inspissated secretions and conditions such as acute or chronic bronchial pulmonary disease, including infectious pneumonia, bronchitis or tracheobronchitis, bronchiectasis, cystic fibrosis, asthma, tuberculosis, and fungal infections. For such therapies, a solution or finely divided dry preparation of the LS-DNase is instilled in conventional fashion into the airways (e.g., bronchi) or lungs of a patient, for example by aerosolization.

LS-DNase also is useful for adjunctive treatment of abscesses or severe closed-space infections in conditions such as empyema, meningitis, abscess, peritonitis, sinusitis, otitis, periodontitis, pericarditis, pancreatitis, cholelithiasis, endocarditis and septic arthritis, as well as in topical treatments in a variety of inflammatory and infected lesions such as infected lesions of the skin and/or mucosal membranes, surgical wounds, ulcerative lesions and burns. LS-DNase may improve the efficacy of antibiotics used in the treatment of such infections (e.g., gentamicin activity is markedly reduced by reversible binding to intact DNA).

LS-DNase also is useful for preventing the new development and/or exacerbation of respiratory infections, such as may occur in patients having cystic fibrosis, chronic bronchitis, asthma, pneumonia, or other pulmonary disease, or patients whose breathing is assisted by ventilator or other mechanical device, or other patients at risk of developing respiratory infections, for example post-surgical patients.

LS-DNase also is useful for the treatment for systemic lupus erythematosus (SLE), a life-threatening autoimmune disease characterized by the production of diverse autoantibodies. DNA is a major antigenic component of the immune complexes. In this instance, the LS-DNase may be given systemically, for example by intravenous, subcutaneous, intrathecal, or intramuscular administration to the affected patient.

Finally, LS-DNase is useful for the treatment of other non-infected conditions in which there is an accumulation of cellular debris that includes cellular DNA, such as pyelonephritis and tubulo-interstitial kidney disease.

LS-DNase can be formulated according to known methods to prepare therapeutically useful compositions. Typically, the LS-DNase is formulated with a physiologically acceptable excipient (or carrier) for therapeutic use. Such excipients are used, for example, to provide liquid formulations and sustained-release formulations of LS-DNase. A preferred therapeutic composition is a solution of LS-DNase in a buffered or unbuffered aqueous solution, and preferably is an isotonic salt solution such as 150 mM sodium chloride containing 1.0 mM calcium chloride at pH 7. These solutions are particularly adaptable for use in commercially-available nebulizers including jet nebulizers and ultrasonic nebulizers useful for administration directly into the airways or lungs of an affected patient. Another preferred therapeutic composition is a dry powder of LS-DNase, preferably prepared by spray-drying of a solution of the LS-DNase, essentially as described in co-pending U.S. patent application Ser. No. 08/206,020 (filed Mar. 4, 1994). In all cases, it is desirable that the therapeutic compositions be sterile. Preferably, the therapeutic compositions are disposed in a container fabricated of plastic or other non-glass material.

In a further embodiment, the therapeutic composition comprises cells actively producing LS-DNase. Such cells may be directly introduced into the tissue of a patient, or may be encapsulated within porous membranes which are then implanted in a patient (see e.g., Aebischer, et al., U.S. Pat. No. 4,892,538, issued Jan. 9, 1990; Aebischer, et al., U.S. Pat. No. 5,283,187, issued Feb. 1, 1994), in either case providing for the delivery of the LS-DNase into areas within the body of the patient in need of increased concentrations of DNA-hydrolytic activity. For example, the patient's own cells could be transformed, either in vivo or ex vivo, with DNA encoding LS-DNase, and then used to produce the LS-DNase directly within the patient. This latter method is commonly referred to as gene therapy.

The therapeutically effective amount of LS-DNase will depend, for example, upon the amount of DNA and actin in the material to be treated, the therapeutic objectives, the route of administration, and the condition of the patient. Accordingly, it will be necessary for the therapist to titer the dosage and modify the route of administration as required to obtain the optimal therapeutic effect. In view of its reduced inhibition by actin and consequential increased DNA-hydrolytic activity in the presence of actin relative to human DNase I, the amount of LS-DNase required to achieve a therapeutic effect may be less than the amount of human DNase I necessary to achieve the same effect under the same conditions. Generally, the therapeutically effective amount of LS-DNase will be a dosage of from about 0.1 $\mu$g to about 5 mg of the variant per kilogram of body weight of the patient, administered within pharmaceutical compositions, as described herein.

LS-DNase optionally is combined with or administered in concert with one or more other pharmacologic agents used to treat the conditions listed above, such as antibiotics, bronchodilators, anti-inflammatory agents, mucolytics (e.g. n-acetyl-cysteine), actin binding or actin severing proteins (e.g., gelsolin; Matsudaira et al., Cell 54:139–140 (1988); Stossel, et al., PCT Patent Publication No. WO 94/22465, published Oct. 13, 1994; protease inhibitors; or gene therapy product (e.g., comprising the cystic fibrosis transmembrane conductance regulator (CFTR) gene); Riordan, et al., Science 245:1066–1073 (1989)).

This invention also provides methods for determining the presence of a nucleic acid molecule encoding LS-DNase in test samples prepared from cells, tissues, or biological fluids, comprising contacting the test sample with isolated DNA comprising all or a portion of the nucleotide coding sequence for LS-DNase and determining whether the isolated DNA hybridizes to a nucleic acid molecule in the test sample. DNA comprising all or a portion of the nucleotide coding sequence for LS-DNase is also used in hybridization assays to identify and to isolate nucleic acids sharing substantial sequence identity to the coding sequence for LS-DNase, such as nucleic acids that encode naturally-occurring allelic variants of LS-DNase.

Also provided is a method for amplifying a nucleic acid molecule encoding LS-DNase that is present in a test sample, comprising the use of an oligonucleotide having a portion of the nucleotide coding sequence for LS-DNase as a primer in a polymerase chain reaction.

The following examples are offered by way of illustration only and are not intended to limit the invention in any manner. All patent and literature references cited herein are expressly incorporated.

EXAMPLE 1

Cloning LS-DNase cDNA

Full-length cDNA encoding LS-DNase was identified by screening a human liver cDNA library (in λ-UniZAP XR, Stratagene, La Jolla, Calif.) with a mixture of the following oligonucleotide probes, each of which had been end-labeled with T4 polynucleotide kinase and 65-$^{32}$P-adenosine triphosphate to a high specific radioactivity:

5'-ACTGTAGTTTAAATTCAACTGGAAAGTGGTCG CTGACATCCAGGG-3' (SEQ. ID. NO: 5)

5'-GATGTCATTGTGAAGGTCATCAAACGCTGTGA CATCATACTCGTG-3' (SEQ. ID. NO: 6)

5'-GTGTTTTCCAGGGGAGCCCTTTGTGGTCTGGT TCCAATCTCCCCA-3' (SEQ. ID. NO: 7)

5'-CTGGAGGTCTCCCAGCACTGGCAGAGCAAGG ACGTGATCCTGCTT-3' (SEQ. ID. NO: 8)

5'-GCCCAGCATCATCGCGAAGTTCCTGGCTGGCT ATCACCTCGCGCT-3' (SEQ. ID. NO: 9)

5'-CCAGTACAAGGAGATGTACCTCTTCGTTTACA GGAAAGACGCCGT-3' (SEQ. ID. NO: 10)

The first three of the oligonucleotide probes listed above (SEQ. ID. NOS: 5–7) comprise portions of the EST sequences having accession codes T68985, T69063, HSAAACIFW, T73558, T61400, T73653, and T61368 in the Genbank database. The other two oligonucleotide probes listed above (SEQ. ID. NOS: 9–10) comprise portions of the EST sequences having accession codes R78020 and H42990 in the Genbank database.

Hybridization of the probes to the cDNA library was carried out under low stringency conditions (in 20% vol/vol formamide, 5×SSPE, 5×Denhardt's solution, 0.1% sodium dodecyl sulfate (SDS), and 100 μg/ml sonicated salmon sperm DNA), at 42° C. Post hybridization washes were carried out in 2×SSC, 0.1% SDS, at 42° C. 1×SSPE is l150 mM NaCl, 10 mM sodium phosphate, 1 mM EDTA, pH 7.4. 1×Denhardt's solution is 0.02% Ficoll, 0.02% bovine serum albumin, and 0.02% polyvinyl-pyrrolidone. 1×SSC is 0.15 M NaCl, 0.015 M sodium citrate, pH 7.0.

Hybridization-positive clones were found only with the first three of the oligonucleotide probes listed above (SEQ. ID. NOS: 5–7). Those clones were converted into phagemid-based sequences following standard procedures (Stratagene, La Jolla, Calif., USA) and were sequenced. The largest inserted nucleotide sequence found amongst the hybridization-positive clones was 1079 base-pairs in length, including an open reading frame of 915 base-pairs that encodes a predicted protein that is 305 amino acid residues in length. The nucleotide sequence of the 1079 base-pair insert (SEQ. ID. NO: 1) and the amino acid sequence of predicted protein (SEQ. ID. NO: 2) are shown in FIG. 1.

The predicted protein includes a signal sequence that is 20 amino acid residues in length. Cleavage of the signal sequence releases the mature protein (LS-DNase), which has a predicted molecular weight of 33,400 Daltons and a predicted pI of 9.7. The amino acid sequence of LS-DNase is 46% identical to the amino acid sequence of human DNase I (FIG. 2).

LS-DNase contains five cysteine residues, two of which (Cys-174 and Cys-211) coincide with a pair of cysteine residues in human DNase I that are disulfide bonded, suggesting that LS-DNase and human DNase I may have similar tertiary structures. Amino acid residues known to be important for the DNA-hydrolytic activity of human DNase I are conserved in LS-DNase, including the active site histidine residues His-135 and His-254. Conversely, several amino acid residues known to comprise the actin-binding site of human DNase I are not conserved in LS-DNase. In particular, Val-67 and Ala-114 of human DNase I are replaced by Ile-69 and Phe-115, respectively, at the homologous positions in LS-DNase. An analogous replacement of Val-67 by Ile occurs in rat DNase I, which has approximately 1000-fold lower affinity for actin as compared to human DNase I.

EXAMPLE 2

Expression of LS-DNase cDNA

The cDNA encoding LS-DNase was subcloned into a mammalian expression vector pRK5 (Gorman, et al., DNA and Protein Engineering Techniques 2:1 (1990); European Patent Publication EP 307,247, published Mar. 15, 1989). The resulting recombinant vector is referred to as pRK5/LS-DNase. Human embryonic kidney 293 cells (American Type Culture Collection, CRL 1573) were grown in serum-containing Dulbecco Modified Eagle's medium (DMEM) to 70% confluency and then transiently transfected with pRK5/LS-DNase, or as a control, pRK5 alone. 24 hours post-transfection, the cells were washed with phosphate buffered saline and transferred to serum-free medium containing insulin. 72–96 hours later, conditioned medium was collected from the cell cultures and concentrated approximately 10-fold. Proteins expressed in the cell cultures were analyzed by SDS-polyacrylamide gel electrophoresis (SDS-PAGE).

Cells transfected with pRK-5/LS-DNase were found to produce a unique, sharply resolving protein of about 32,000–34,000 Daltons, that was not produced in cells transfected with pRK5 alone. The molecular weight size of this protein is in good agreement with that predicted for LS-DNase.

EXAMPLE 3

Biological Activity of LS-DNase

Concentrated cell culture supernatants, prepared as described above, were tested for DNase activity in a hyperchromicity assay (Kunitz, J. Gen. Physiol. 33:349–362 (1950); Kunitz, J. Gen. Physiol. 33:363–377 (1950)), and a methyl green assay (Kurnick, Arch. Biochem. 29:41–53 (1950); Sinicropi, et al., Anal. Biochem. 222:351–358 (1994)). In both assays, DNase activity was detected in the supernatants from cells transfected with pRK5/LS-DNase, but not in the supernatants from cells transfected with pRK5 alone.

EXAMPLE 4

Resistance to Actin Inhibition

To determine whether the DNA-hydrolytic activity of LS-DNase is inhibited by actin, a plasmid nicking assay was used. This assay measures the conversion of supercoiled double-stranded pBR322 plasmid DNA to nicked, linear, and degraded forms. Specifically, various DNase samples were added to 20 μl of solution containing 25 μg/ml supercoiled double-stranded pBR322 DNA in 25 mM HEPES buffer, 1 mM $MgCl_2$, 1 mM $CaCl_2$, 100 μg/ml bovine serum albumin, and the samples were incubated for 10 minutes at 21° C. To determine inhibition by actin, the DNase samples were pre-incubated with actin for 15 minutes at 21° C. prior to being added to the solution of pBR322 DNA. Reactions were stopped by the addition of EDTA to a final concentration of 10 mM, together with xylene cyanol, bromphenol blue, and glycerol. The integrity of the pBR322 DNA was analyzed by electrophoresis of the reaction mixtures on 0.8 weight/vol. agarose gels. After electrophoresis, the gels were stained with a solution of ethidium bromide and the DNA in the gels was visualized by ultraviolet light.

As expected, human DNase I converted the starting plasmid DNA to degraded forms, and the DNA-hydrolytic activity of human DNase I was inhibited by added actin in a concentration-dependent manner. LS-DNase converted the starting plasmid DNA to nicked, linear, and degraded forms, but the DNA-hydrolytic activity of LS-DNase was not inhibited by concentrations of actin that fully inhibited human DNase I.

EXAMPLE 5

Pattern of Expression of LS-DNase in Human Tissue

Northern blots of various human tissues were performed using a radiolabeled probe comprising a portion of the coding sequence of the cloned LS-DNase cDNA. Expression of LS-DNase messenger RNA (mRNA) was found to be highest in liver and spleen. LS-DNase mRNA either was poorly expressed or not expressed in other tissues examined. No LS-DNase mRNA was detectable in pancreas tissue.

Northern blots of various human tissues also were performed using a radiolabeled probe comprising a portion of the nucleotide coding sequence for human DNase I. In contrast to LS-DNase mRNA, human DNase I mRNA appeared to be exclusively expressed in pancreas tissue.

EXAMPLE 6

Cloning of LS-DNase Variant

A 649 base-pair EcoRI-PstI fragment of the coding sequence of the cloned LS-DNase cDNA was used to screen a murine liver cDNA library (in λ-gt10, Clontech, Palo Alto, Calif., USA). From about two million clones screened, more than 60 hybridization positive clones were identified. Partial sequencing of six random positive clones showed that they all originated from the same gene. The inserted nucleotide sequence of one of those positive clones was completely sequenced. The insert was 1124 base-pairs in length, including an open reading frame of 930 base-pairs that encodes a predicted protein, referred to as murine LS-DNase, that is 310 amino acid residues in length.

The nucleotide sequence of the 1124 base-pair insert (SEQ. ID. NO: 11) is shown in FIG. 3. The open reading frame begins with the ATG codon at nucleotide 173 and continues to the stop codon at nucleotide 1103. The first 75 nucleotides of the open reading frame (the first 25 amino acid residues of the predicted protein) encode a putative signal sequence. Accordingly, the predicted murine mature LS-DNase protein is 285 amino acid residues in length, has a molecular weight of 33,100 Daltons and a predicted pI of 9.4. The amino acid sequence of the murine mature LS-DNase is 84% identical to the amino acid sequence shown in FIG. 1 for human mature LS-DNase.

Northern blots of various mouse tissues were performed using a radiolabeled probe comprising a portion of the nucleotide coding sequence for murine LS-DNase. Expression of murine LS-DNase messenger RNA (mRNA) was found to be highest in liver and spleen. LS-DNase mRNA either was poorly expressed or not expressed in other tissues examined.

What is claimed is:

1. An isolated nucleic acid molecule comprising a nucleotide sequence encoding the amino acid sequence shown in FIG. 1 for mature LS-DNase.

2. An expression vector comprising a nucleotide sequence encoding the amino acid sequence shown in FIG. 1 for mature LS-DNase operably linked to a promoter recognized by a host cell transformed with the vector.

3. An isolated nucleic acid molecule comprising a nucleotide sequence that encodes an amino acid sequence having at least 95% identity with the amino acid sequence shown in FIG. 1 for mature LS-DNase.

4. An isolated nucleic acid molecule comprising a nucleotide sequence that encodes an amino acid sequence that differs from the amino acid sequence shown in FIG. 1 for mature LS-DNase by the substitution of one amino acid for another at only a single position within the FIG. 1 sequence.

5. An isolated nucleic acid molecule comprising a nucleotide sequence that encodes an amino acid sequence that differs from the amino acid sequence shown in FIG. 1 for mature LS-DNase by the substitution of one amino acid for another at only two positions within the FIG. 1 sequence.

6. A host cell transformed with an expression vector comprising a nucleotide sequence encoding the amino acid sequence shown in FIG. 1 for mature LS-DNase.

7. A process which comprises transforming a host cell with a nucleic acid molecule that encodes a polypeptide comprising the amino acid sequence shown in FIG. 1 for mature LS-DNase and culturing the host cell under conditions such that the polypeptide is produced in the host cell.

\* \* \* \* \*

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 1079 base pairs
      (B) TYPE: Nucleic Acid
      (C) STRANDEDNESS: Single
      (D) TOPOLOGY: Linear (xi) SEQUENCE DESCRIPTION: SEQ ID NO: 1:

```
GAATTCGGCA CGAGAGCACT CCAAGCACTG CTGTCTTCTC ACAGAGTCTT          50

GAAGCCAGAG CAGCGCCAGG ATGTCACGGG AGCTGGCCCC ACTGCTGCTT         100

CTCCTCCTCT CCATCCACAG CGCCCTGGCC ATGAGGATCT GCTCCTTCAA         150

CGTCAGGTCC TTTGGGGAAA GCAAGCAGGA AGACAAGAAT GCCATGGATG         200
```

-continued

```
TCATTGTGAA GGTCATCAAA CGCTGTGACA TCATACTCGT GATGGAAATC        250

AAGGACAGCA ACAACAGGAT CTGCCCCATA CTGATGGAGA AGCTGAACAG        300

AAATTCAAGG AGAGGCATAA CGTACAACTA TGTGATTAGC TCTCGGCTTG        350

GAAGAAACAC ATATAAAGAA CAATATGCCT TTCTCTACAA GGAAAAGCTG        400

GTGTCTGTGA AGAGGAGTTA TCACTACCAT GACTATCAGG ATGGAGACGC        450

AGATGTGTTT TCCAGGGAGC CCTTTGTGGT CTGGTTCCAA TCTCCCCACA        500

CTGCTGTCAA AGACTTCGTG ATTATCCCCC TGCACACCAC CCCAGAGACA        550

TCCGTTAAGG AGATCGATGA GTTGGTTGAG GTCTACACGG ACGTGAAACA        600

CCGCTGGAAG GCGGAGAATT TCATTTTCAT GGGTGACTTC AATGCCGGCT        650

GCAGCTACGT CCCCAAGAAG GCCTGGAAGA ACATCCGCTT GAGGACTGAC        700

CCCAGGTTTG TTTGGCTGAT CGGGGACCAA GAGGACACCA CGGTGAAGAA        750

GAGCACCAAC TGTGCATATG ACAGGATTGT GCTTAGAGGA CAAGAAATCG        800

TCAGTTCTGT TGTTCCCAAG TCAAACAGTG TTTTTGACTT CCAGAAAGCT        850

TACAAGCTGA CTGAAGAGGA GGCCCTGGAT GTCAGCGACC ACTTTCCAGT        900

TGAATTTAAA CTACAGTCTT CAAGGGCCTT CACCAACAGC AAAAAATCTG        950

TCACTCTAAG GAAGAAAACA AAGAGCAAAC GCTCCTAGAC CCAAGGGTCT       1000

CATCTTATTA ACCATTTCTT GCCTCTAAAT AAAATGTCTC TAACAAAAAA       1050

AAAAAAAAAA AAAAAAAAAA AAACTCGAG                              1079
```

(2) INFORMATION FOR SEQ ID NO: 2:

(i) SEQUENCE CHARACTERISTICS:
        (A) LENGTH: 305 amino acids
        (B) TYPE: Amino Acid
        (D) TOPOLOGY: Linear (xi) SEQUENCE DESCRIPTION: SEQ ID NO: 2:

```
Met Ser Arg Glu Leu Ala Pro Leu Leu Leu Leu Leu Leu Ser Ile
 1               5                  10                  15

His Ser Ala Leu Ala Met Arg Ile Cys Ser Phe Asn Val Arg Ser
                20                  25                  30

Phe Gly Glu Ser Lys Gln Glu Asp Lys Asn Ala Met Asp Val Ile
                35                  40                  45

Val Lys Val Ile Lys Arg Cys Asp Ile Ile Leu Val Met Glu Ile
                50                  55                  60

Lys Asp Ser Asn Asn Arg Ile Cys Pro Ile Leu Met Glu Lys Leu
                65                  70                  75

Asn Arg Asn Ser Arg Arg Gly Ile Thr Tyr Asn Tyr Val Ile Ser
                80                  85                  90

Ser Arg Leu Gly Arg Asn Thr Tyr Lys Glu Gln Tyr Ala Phe Leu
                95                 100                 105

Tyr Lys Glu Lys Leu Val Ser Val Lys Arg Ser Tyr His Tyr His
               110                 115                 120

Asp Tyr Gln Asp Gly Asp Ala Asp Val Phe Ser Arg Glu Pro Phe
               125                 130                 135

Val Val Trp Phe Gln Ser Pro His Thr Ala Val Lys Asp Phe Val
               140                 145                 150

Ile Ile Pro Leu His Thr Thr Pro Glu Thr Ser Val Lys Glu Ile
               155                 160                 165
```

-continued

```
Asp Glu Leu Val Glu Val Tyr Thr Asp Val Lys His Arg Trp Lys
            170                 175                 180

Ala Glu Asn Phe Ile Phe Met Gly Asp Phe Asn Ala Gly Cys Ser
            185                 190                 195

Tyr Val Pro Lys Lys Ala Trp Lys Asn Ile Arg Leu Arg Thr Asp
            200                 205                 210

Pro Arg Phe Val Trp Leu Ile Gly Asp Gln Glu Asp Thr Thr Val
            215                 220                 225

Lys Lys Ser Thr Asn Cys Ala Tyr Asp Arg Ile Val Leu Arg Gly
            230                 235                 240

Gln Glu Ile Val Ser Ser Val Pro Lys Ser Asn Ser Val Phe
            245                 250                 255

Asp Phe Gln Lys Ala Tyr Lys Leu Thr Glu Glu Ala Leu Asp
            260                 265                 270

Val Ser Asp His Phe Pro Val Glu Phe Lys Leu Gln Ser Ser Arg
            275                 280                 285

Ala Phe Thr Asn Ser Lys Lys Ser Val Thr Leu Arg Lys Lys Thr
            290                 295                 300

Lys Ser Lys Arg Ser
            305
```

(2) INFORMATION FOR SEQ ID NO: 3:

(i) SEQUENCE CHARACTERISTICS:
        (A) LENGTH: 285 amino acids
        (B) TYPE: Amino Acid
        (D) TOPOLOGY: Linear (xi) SEQUENCE DESCRIPTION: SEQ ID NO: 3:

```
Met Arg Ile Cys Ser Phe Asn Val Arg Ser Phe Gly Glu Ser Lys
 1               5                  10                  15

Gln Glu Asp Lys Asn Ala Met Asp Val Ile Val Lys Val Ile Lys
            20                  25                  30

Arg Cys Asp Ile Ile Leu Val Met Glu Ile Lys Asp Ser Asn Asn
            35                  40                  45

Arg Ile Cys Pro Ile Leu Met Glu Lys Leu Asn Arg Asn Ser Arg
            50                  55                  60

Arg Gly Ile Thr Tyr Asn Tyr Val Ile Ser Ser Arg Leu Gly Arg
            65                  70                  75

Asn Thr Tyr Lys Glu Gln Tyr Ala Phe Leu Tyr Lys Glu Lys Leu
            80                  85                  90

Val Ser Val Lys Arg Ser Tyr His Tyr His Asp Tyr Gln Asp Gly
            95                  100                 105

Asp Ala Asp Val Phe Ser Arg Glu Pro Phe Val Val Trp Phe Gln
            110                 115                 120

Ser Pro His Thr Ala Val Lys Asp Phe Val Ile Ile Pro Leu His
            125                 130                 135

Thr Thr Pro Glu Thr Ser Val Lys Glu Ile Asp Glu Leu Val Glu
            140                 145                 150

Val Tyr Thr Asp Val Lys His Arg Trp Lys Ala Glu Asn Phe Ile
            155                 160                 165

Phe Met Gly Asp Phe Asn Ala Gly Cys Ser Tyr Val Pro Lys Lys
            170                 175                 180

Ala Trp Lys Asn Ile Arg Leu Arg Thr Asp Pro Arg Phe Val Trp
            185                 190                 195
```

```
Leu Ile Gly Asp Gln Glu Asp Thr Thr Val Lys Lys Ser Thr Asn
                200                 205                 210

Cys Ala Tyr Asp Arg Ile Val Leu Arg Gly Gln Glu Ile Val Ser
                215                 220                 225

Ser Val Val Pro Lys Ser Asn Ser Val Phe Asp Phe Gln Lys Ala
                230                 235                 240

Tyr Lys Leu Thr Glu Glu Glu Ala Leu Asp Val Ser Asp His Phe
                245                 250                 255

Pro Val Glu Phe Lys Leu Gln Ser Ser Arg Ala Phe Thr Asn Ser
                260                 265                 270

Lys Lys Ser Val Thr Leu Arg Lys Lys Thr Lys Ser Lys Arg Ser
                275                 280                 285

(2) INFORMATION FOR SEQ ID NO: 4:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO: 4:

Leu Lys Ile Ala Ala Phe Asn Ile Gln Thr Phe Gly Glu Thr Lys
  1              5                  10                  15

Met Ser Asn Ala Thr Leu Val Ser Tyr Ile Val Gln Ile Leu Ser
                 20                  25                  30

Arg Tyr Asp Ile Ala Leu Val Gln Glu Val Arg Asp Ser His Leu
                 35                  40                  45

Thr Ala Val Gly Lys Leu Leu Asp Asn Leu Asn Gln Asp Ala Pro
                 50                  55                  60

Asp Thr Tyr His Tyr Val Val Ser Glu Pro Leu Gly Arg Asn Ser
                 65                  70                  75

Tyr Lys Glu Arg Tyr Leu Phe Val Tyr Arg Pro Asp Gln Val Ser
                 80                  85                  90

Ala Val Asp Ser Tyr Tyr Tyr Asp Asp Gly Cys Glu Pro Cys Gly
                 95                 100                 105

Asn Asp Thr Phe Asn Arg Glu Pro Ala Ile Val Arg Phe Phe Ser
                110                 115                 120

Arg Phe Thr Glu Val Arg Glu Phe Ala Ile Val Pro Leu His Ala
                125                 130                 135

Ala Pro Gly Asp Ala Val Ala Glu Ile Asp Ala Leu Tyr Asp Val
                140                 145                 150

Tyr Leu Asp Val Gln Glu Lys Trp Gly Leu Glu Asp Val Met Leu
                155                 160                 165

Met Gly Asp Phe Asn Ala Gly Cys Ser Tyr Val Arg Pro Ser Gln
                170                 175                 180

Trp Ser Ser Ile Arg Leu Trp Thr Ser Pro Thr Phe Gln Trp Leu
                185                 190                 195

Ile Pro Asp Ser Ala Asp Thr Thr Ala Thr Pro Thr His Cys Ala
                200                 205                 210

Tyr Asp Arg Ile Val Val Ala Gly Met Leu Leu Arg Gly Ala Val
                215                 220                 225

Val Pro Asp Ser Ala Leu Pro Phe Asn Phe Gln Ala Ala Tyr Gly
                230                 235                 240

Leu Ser Asp Gln Leu Ala Gln Ala Ile Ser Asp His Tyr Pro Val
                245                 250                 255
```

Glu Val Met Leu Lys
                260

(2) INFORMATION FOR SEQ ID NO: 5:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO: 5:

ACTGTAGTTT AAATTCAACT GGAAAGTGGT CGCTGACATC CAGGG                45

(2) INFORMATION FOR SEQ ID NO: 6:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO: 6:

GATGTCATTG TGAAGGTCAT CAAACGCTGT GACATCATAC TCGTG                45

(2) INFORMATION FOR SEQ ID NO: 7:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

GTGTTTTCCA GGGGAGCCCT TTGTGGTCTG GTTCCAATCT CCCCA                45

(2) INFORMATION FOR SEQ ID NO: 8:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

CTGGAGGTCT CCCAGCACTG GCAGAGCAAG GACGTGATCC TGCTT                45

(2) INFORMATION FOR SEQ ID NO: 9:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO: 9:

GCCCAGCATC ATCGCGAAGT TCCTGGCTGG CTATCACCTC GCGCT                45

(2) INFORMATION FOR SEQ ID NO: 10:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO: 10:

-continued

```
CCAGTACAAG GAGATGTACC TCTTCGTTTA CAGGAAAGAC GCCGT              45
```

(2) INFORMATION FOR SEQ ID NO: 11:

(i) SEQUENCE CHARACTERISTICS:
        (A) LENGTH: 1124 base pairs
        (B) TYPE: Nucleic Acid
        (C) STRANDEDNESS: Single
        (D) TOPOLOGY: Linear (xi) SEQUENCE DESCRIPTION: SEQ ID NO: 11:

```
GAATTCCGGC CCATTACCTT CATTTCCTTG GGGATTGAAA CGCGTGATGG          50

TGAGTTCCTC AGAGAAGTGA AAGTGACCTA GAGGGATCCA GTAATTCCTG         100

TTATCAGCCT GCTTTATAAG TCAGTGAGCC AGGCACTGTC TTCATCCAGC         150

CTGAAGTCCC AGGAGTGCAA AGATGTCCCT GCACCCAGCT TCCCCACGCC         200

TGGCCTCCCT GCTGCTCTTC ATCCTTGCCC TCCATGACAC CCTGGCCCTA         250

AGGCTCTGCT CCTTCAATGT GAGGTCCTTT GGAGCGAGCA AGAAGGAAAA         300

CCATGAAGCC ATGGATATCA TTGTGAAGAT CATCAAACGC TGTGACCTTA         350

TACTGTTGAT GGAAATCAAG GACAGCAGCA ACAACATCTG TCCCATGCTG         400

ATGGAGAAGC TGAATGGAAA TTCACGAAGA AGCACAACAT ACAACTATGT         450

GATTAGTTCT CGACTTGGAA GAAACACGTA CAAAGAGCAG TATGCCTTCG         500

TCTACAAGGA GAAGCTGGTG TCTGTGAAGA CAAAATACCA CTACCATGAC         550

TATCAGGATG GAGACACAGA CGTGTTTTCC AGGGAGCCCT TTGTGGTTTG         600

GTTCCATTCC CCCTTTACTG CTGTCAAGGA CTTCGTGATT GTCCCCTTGC         650

ACACAACTCC CGAGACCTCC GTTAAAGAGA TAGATGAGCT GGTCGATGTC         700

TACACGGATG TGAGAAGCCA GTGGAAGACA GAGAATTTCA TCTTCATGGG         750

TGATTTCAAC GCCGGCTGTA GCTATGTCCC CAAGAAGGCC TGGCAGAACA         800

TTCGTTTGAG GACGGACCCC AAGTTTGTTT GGCTGATTGG GGACCAAGAG         850

GACACTACGG TCAAGAAGAG TACCAGCTGT GCCTATGACA GGATTGTGCT         900

TTGTGGACAA GAGATAGTCA ACTCCGTGGT TCCCCGTTCC AGTGGCGTCT         950

TTGACTTTCA GAAAGCTTAT GACTTGTCTG AGGAGGAGGC CCTGGATGTC        1000

AGTGATCACT TTCCAGTTGA GTTTAAGCTA CAGTCTTCAA GGGCCTTCAC        1050

CAACAACAGA AAATCTGTTT CTCTCAAAAA GAGAAAAAAA GGCAATCGCT        1100

CCTAGGTATC ACGCTCCGGA ATTC                                   1124
```